US00PP26539P3

(12) United States Plant Patent
Ranney

(10) Patent No.: US PP26,539 P3
(45) Date of Patent: Mar. 29, 2016

(54) INTERSPECIFIC HYBRID FLOWERING PEAR 'NCPX1'

(50) Latin Name: ***Pyrus calleryana*×*Pyrus pyrifolia***
Varietal Denomination: NCPX1

(71) Applicant: North Carolina State University, Raleigh, NC (US)

(72) Inventor: Thomas G. Ranney, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 147 days.

(21) Appl. No.: 13/999,897

(22) Filed: Apr. 1, 2014

(65) Prior Publication Data

US 2015/0282401 P1 Oct. 1, 2015

(51) Int. Cl.
*A01H 5/00* (2006.01)

(52) U.S. Cl.
USPC ..... Plt./177

(58) Field of Classification Search
USPC ..... Plt./177
See application file for complete search history.

*Primary Examiner* — Annette Para

(74) *Attorney, Agent, or Firm* — Myers Bigel Sibley & Sajovec, P.A.

(57) ABSTRACT

'NCPX1' is a new cultivar of hybrid flowering pear with a narrow fastigiated habit, red to purple flower buds opening with white flower petals and a high level of resistance to fire blight.

3 Drawing Sheets

Latin name of the genus and species: The Latin name of the novel plant variety disclosed herein is *Pyrus calleryana*× *Pyrus pyrifolia*.

Variety denomination: The inventive interspecific hybrid of *Pyrus calleryana*×*Pyrus pyrifolia* disclosed herein has been given the varietal denomination 'NCPX1'.

BACKGROUND OF THE INVENTION

The present invention comprises a new and distinct hybrid flowering pear cultivar hereinafter referred to by the cultivar name 'NCPX1'. This new flowering pear was developed through a breeding program at North Carolina State University, Mills River, N.C. 'NCPX1' was selected from an $F_1$ population of seedlings grown from a controlled cross of *Pyrus calleryana* 'Cleveland Select'×*Pyrus pyrifolia* 'Ohara Beni'. The first asexual propagation of 'NCPX1' was carried out in August 2007 by budding at the North Carolina State University, Mountain Horticultural Crops Research Station, Mills River, N.C. and has been asexually reproduced repeatedly by budding over a 7 year period. 'NCPX1' propagates readily from budding using chip budding in mid-summer. 'NCPX1' has been found to retain its distinctive characteristics through successive asexual propagations.

SUMMARY OF THE INVENTION

The following are the unique and distinguishing characteristics of this new cultivar when grown under standard horticultural practices at North Carolina State University, Mountain Horticultural Crops Research Station, Mills River, N.C.

1. Unique fastigiate form.
2. Red to purple flower buds that open with white petals.
3. Resistance to fire blight.

BRIEF DESCRIPTION OF THE DRAWINGS

This new flowering pear is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new dogwood.

DETAILED BOTANICAL DESCRIPTION

Figure 1:
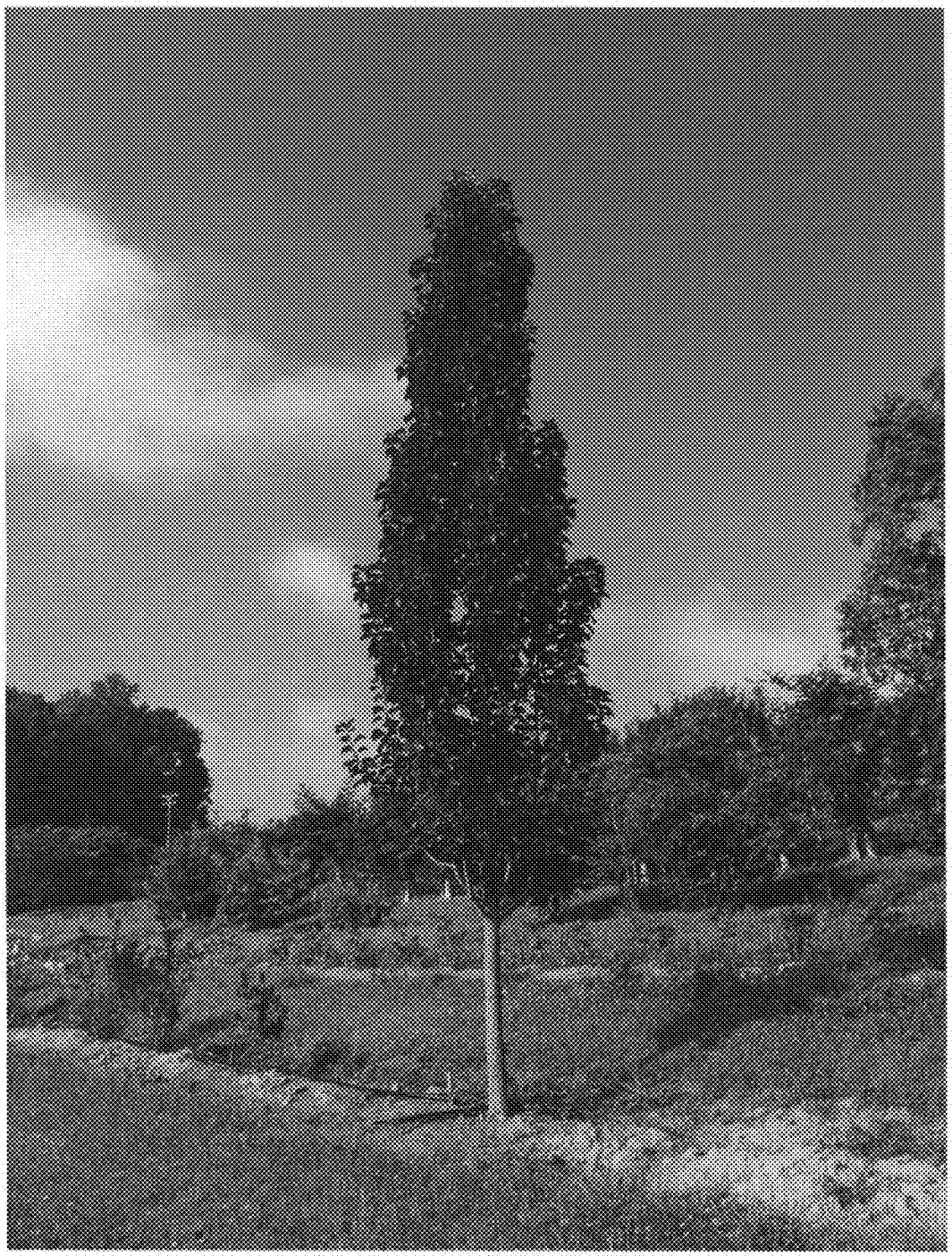
FIG. 1 is a photograph demonstrating the fastigiate form in July 2010.
Figure 2:
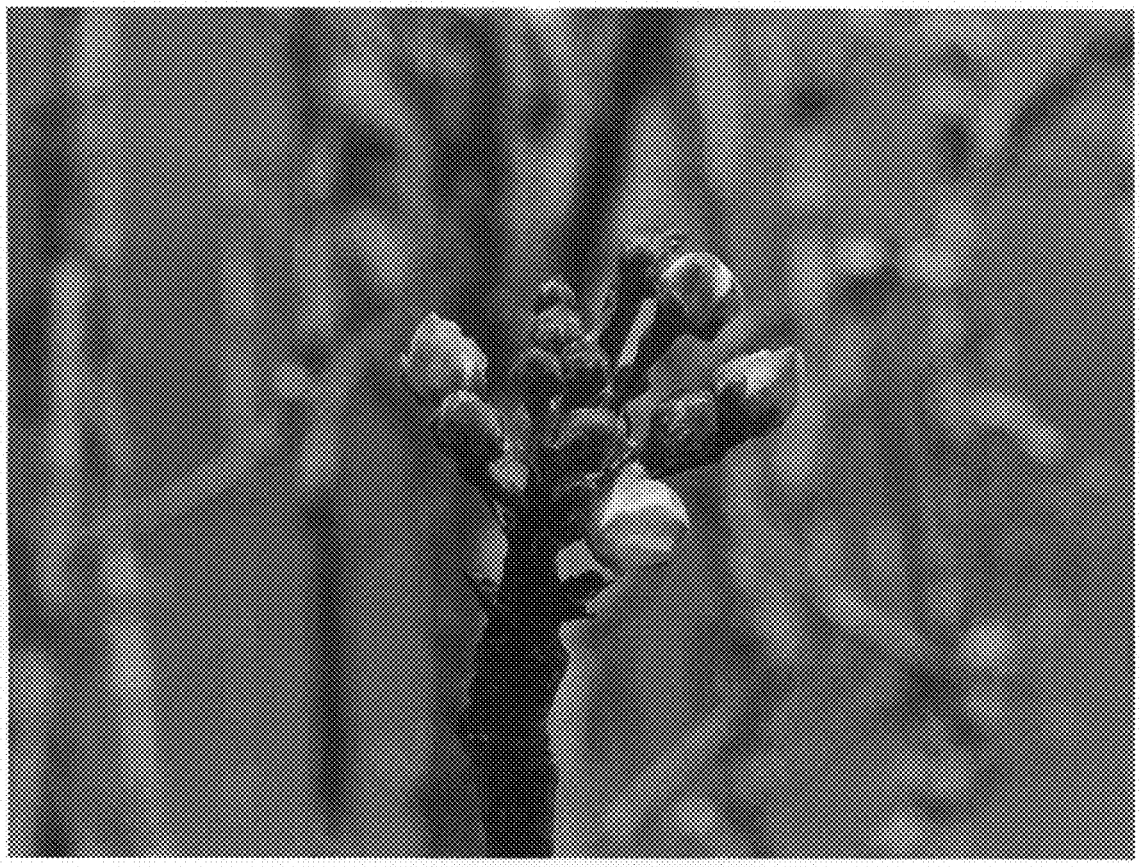
FIG. 2 is a photograph showing the pink to red flower buds in April 2013.
Figure 3:
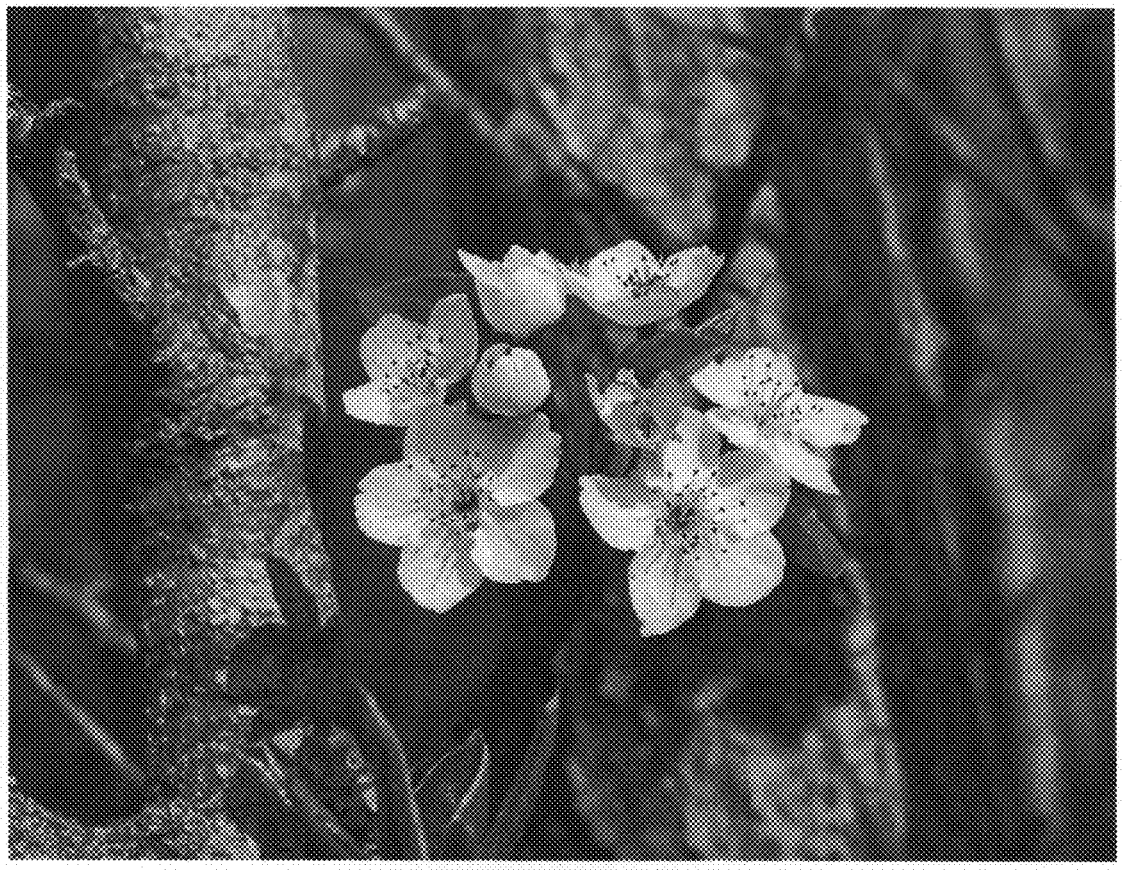
FIG. 3 is a photograph showing the white petal color of flowers near anthesis in April 2013.

The following is a detailed description of the botanical characteristics of the new and distinct variety of interspecific hybrid flowering pear known by the denomination 'NCPX1'. The detailed description was taken on the original eight-year-old tree growing in Mills River, N.C. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety

Classification:

*Botanical name.*—*Pyrus* 'NCPX1'.

*Common name.*—Hybrid flowering pear.

Parentage: $F_1$ hybrid of *Pyrus calleryana* 'Cleveland Select'× *Pyrus pyrifolia* 'Ohara Beni'.

Plant description:

*Growth habit.*—Fastigate and narrow. Height: 25 ft. after 8 years. Width: 6 to 8 ft. after 8 years.

*Shoots and stems.*—Branching habit: upright. Lateral branch length: 8-12 ft. Diameter: 1-4 in. Internode length: 0.8-1.2 in. Color: Greyed-purple (187). Trunk texture: Smooth to rough. Trunk color: Grey-orange (197C).

*Mature leaves.*—Type: Simple. Persistance: Deciduous. Arrangement: Alternate. Shape: Ovate. Apex: Acuminate. Base: Rounded. Veination: Pinnate. Margin: Serrulate. Texture: Glabrous both upper and lower.

*Emerging leaves.*—Color: Upper surface: yellow-green (146A). Lower surface: yellow-green (146A).

*Mature leaves during growing season.*—Color: Upper: green (136A). Lower: yellow-green (147B). Length of lamina: 4 in. Width: 2.4-3.2 in. Petiole: Length: 1.2-2.4 in. Width: 1.2-1.8 in. Color: Grey-purple (187).

*Mature leaves, fall color.*—Mostly dark purple (N186D) or red (45A) with some yellow-orange (31A).

*Inflorescence.*—Bud length: 0.4-0.5 in. Bud diameter: 0.3-0.35 in. Bud shape: Ovate. Bud color: 155A, 63A on tip.

*Individual flowers.*—Diameter: 1.1-1.3 in. Depth: 0.35-0.39 in. Stamen: Number: 19-22. Anther color: Purplish (63A). Filament color: White (N155B). Pistil: Number: 3-4. Stigma: Shape: Linear. Color: Light green (193A). Style: Length: 5-6 mm. Color: Light green (193A). Ovary: Color: Grey-green (194B). Petals: Arrangement: Star. Number: 5 petals. Shape: Elliptic. Margin: Entire. Tip: Obtuse. Length (at anthesis): 0.5-0.55 in. Width (at anthesis): 0.4-0.5 in. Color in bud: Red purple (53C to 63A). Color when opening: Upper: White (N155A) with some pink blush (63A). Lower: White (N155A) with some pink blush (58C to 65A). Color fully opened: Upper: White (155B). Under: White (155B) with some light pink blush (65C).

*Fruit.*—Pome: 4 locules. Size: 0.5-1.0 in. diameter. Shape: Round to ovoid. Color: Gray orange to gray brown (including 177B, N199B, N199D). Lenticels: Many small, circular on surface. Calyx: Mostly deciduous. Length: 0.1-0.11 in. Diameter: 0.08-0.1 in. Pedicel: Length: 0.55-1 in. Diameter: 0.03-0.05 in. Color: Green (132B).

Disease and insect resistance: No significant disease or insect pests have been observed. 'NCPX1' was found to have a high level of resistance to fire blight.

Cold hardiness: At least USDA zone 6b; testing has not been completed in colder zones.

COMPARISON WITH PARENTAL TAXA

Disease resistance to fire blight was evaluated following the procedures of Bell, A. C., T. G. Ranney, T. A. Eaker, and T. B. Sutton, 2004, Resistance to fire blight among flowering pears and quince, *HortScience* 40(2):413-415. Briefly, a virulent strain of *Erwinia amylovora* (E2002a) was prepared from 24 hour old cultures grown on nutrient agar. Three actively growing shoots were inoculated in May of 2011 and 2012 by bisecting the youngest leaves with a pair of scissors that had been dipped into the inoculum prior to each cut. The diseases lesion length and total length of the current season's growth of the inoculated shoot were measured 40 days following inoculation. The severity of infection was expressed as the length of the fire blight lesion as a percentage of overall shoot length. 'NCPX1' was found to have a high level of resistance to fire blight with 0% lesion lengths in both 2011 and 2012 following controlled inoculations (Table 1). No signs or symptoms of fire blight have been observed on 'NCPX1' as the result of natural infection over the last 8 years.

TABLE 1

Comparison of fire blight resistance among 'NCPX1' and parental taxa.

| | Disease severity-2011 (% lesion length) | | Disease severity-2012 (% lesion length) | |
|---|---|---|---|---|
| Cultivar | Range | Mean | Range | Mean |
| 'Ohara Beni' | 60-100 | 86.7 | 100-100 | 100 |
| 'Cleveland Select' | 0-19 | 6.3 | 0-20 | 6.6 |
| 'NCPX1' | 0-0 | 0 | 0-0 | 0 |

Table 2, below, shows additional distinguishing morphological characteristics between 'NCPX1' and its parental taxa.

TABLE 2

Comparison of 'NCPX1' with parental taxa.

| | Taxa | | | |
|---|---|---|---|---|
| Trait | *Pyrus calleryana* 'Cleveland Select' (unpatented) | *Pyrus pyrifolia* 'Ohara Beni' (unpatented) | *Pyrus* 'NCPX1' | *Pyrus* 'Silver Ball' (unpatented) |
| Tree growth Habit | Upright pyramidal | Upright columner. | Very narrow fastigate | Compact, round, dwarf |
| Tree Height (after 8 years) | 25 ft. | 25 ft. | 25 ft. | 12 ft. |
| Tree Width (after 8 years) | 20 ft | 15 ft. | 6 to 8 ft. | 12 ft. |
| Flower bud color | White (N155A) | Red purple (53C to 63A) | Red purple (53C to 63A) | Green white (157B) |
| Flower petal color when opening | White (N155A) | White (N155A) with some pink blush (63A, 58C, and 65A) | White (N155A) with some pink blush (63A, 58C, and 65A) | Green white (157D) |
| Flower petals when fully opened | White (N155A), 0.4 to 0.75 in. in diameter | White (N155A), 1 to 1.3 in. in diameter | White/pink (155B) 1.2 to 1.4 in. in diameter | White (N155) 0.4 to 1.0 in. in diameter |

'NCPX1' is distinguished from *Pyrus calleryana* 'Cleveland Select' in that 'NCPX1' has a narrower, fastigiate habit, red to purple flower buds, and larger flower diameter. 'NCPX1' is distinguished from *Pyrus pyrifolia* 'Ohara Beni' in that it has a narrower, fastigiate habit, and superior fire blight resistance. 'NCPX1' is distinguished from *Pyrus* 'Silver Ball' in that it 'NCPX1' is taller and more columnar with red to purple flower buds.

What is claimed is:

1. A new and distinct interspecific hybrid flowering pear tree named 'NCPX1' as illustrated and described herein.

* * * * *